(12) United States Patent
Kaul et al.

(10) Patent No.: US 10,067,135 B2
(45) Date of Patent: Sep. 4, 2018

(54) MULTIPLEX HEPATITIS B ASSAY

(71) Applicant: Bio-Rad Laboratories, Inc., Hercules, CA (US)

(72) Inventors: Ravi Kaul, Davis, CA (US); Weiming Zheng, Emeryville, CA (US); Roger Walker, Benicia, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/897,040

(22) Filed: Feb. 14, 2018

(65) Prior Publication Data

US 2018/0172687 A1    Jun. 21, 2018

Related U.S. Application Data

(62) Division of application No. 14/261,525, filed on Apr. 25, 2014, now Pat. No. 9,927,439.

(60) Provisional application No. 61/816,518, filed on Apr. 26, 2013.

(51) Int. Cl.

| | |
|---|---|
| *C12Q 1/68* | (2018.01) |
| *C12Q 1/70* | (2006.01) |
| *A61K 39/00* | (2006.01) |
| *A61K 38/00* | (2006.01) |
| *C07H 21/04* | (2006.01) |
| *G01N 33/576* | (2006.01) |
| *G01N 33/543* | (2006.01) |

(52) U.S. Cl.
CPC ... *G01N 33/5761* (2013.01); *G01N 33/54326* (2013.01)

(58) Field of Classification Search
CPC .................. C12Q 1/6818; C12Q 1/706; C12Q 2525/101; C12Q 2525/113; C12Q 2525/204

See application file for complete search history.

*Primary Examiner* — Barry A Chestnut
(74) *Attorney, Agent, or Firm* — Kilpatrick Townsend & Stockton LLP (57) ABSTRACT

Provided herein are multiplex assays for determining whether an individual is or has been infected with Hepatitis B virus, and the stage of infection or resolution. In addition, the multiplex system can discriminate between vaccinated subjects and subjects susceptible to Hepatitis B infection.

19 Claims, 1 Drawing Sheet

MULTIPLEX HEPATITIS B ASSAY

CROSS-REFERENCE TO RELATED PATENT APPLICATIONS

The present patent application is a divisional application of U.S. patent application Ser. No. 14/261,525, filed on Apr. 25, 2014, which claims benefit of priority to U.S. Provisional Patent Applictaion No. 61/816,518, filed on Apr. 26, 2013, both of which are herein incorporated by reference in their entirety for all purposes.

BACKGROUND OF THE INVENTION

Hepatitis B virus causes liver disease. A significant proportion of infected patients develop chronic hepatitis leading to liver damage and subsequent hepatocarcinoma. Hepatitis B infection is characterized by several distinctive serological and immunological responses. The temporal profiles of infection can serve as a useful guide to monitoring the course of disease and also provide serological correlation with the disease's progress (see, e.g., Elgouhari (2008) *Cleveland Clinic J. Med.* 75:881 and Juszczyk (2010) *Vaccine* 18:S23)

Hepatitis B virus contains two major viral proteins, the surface antigen (HBsAg) and the core antigens (HBcAg). Upon infection, HBsAg becomes detectable first, followed by the appearance of anti-HBc IgM generated by the host. Anti-HBs antibodies appear months after the disappearance of HBsAg, and remain detectable indefinitely. During the "window period" (when there is gap of 16-32 weeks between the appearance of HBsAg and the appearance of anti-HBs), the presence of anti-HBc provides serological evidence of current or recent HBV infection. However, presence of anti-HBc IgM and anti-HBc (IgM and IgG) does not indicate either the resolution of infection or protective immunity. The appearance of anti-HBs and the absence of HBsAg indicate the resolution of infection and protective immunity. Furthermore, the presence of anti-HBs in the absence of HBsAg and anti-HBc is indicative of a successfully vaccinated individual.

Hepatitis B serological testing involves measurement of several hepatitis B virus-specific antigens and antibodies. The ability to follow the course of HBV infection and differentiate, e.g., between infection, exposure, and resolution, is important for clinical management. All commercially available Hepatitis B antibody test kits perform one test at a time per reaction vessel. The result of any one given test cannot predict the course or stage of Hepatitis B infection or resolution, so multiple tests must be run, which wastes time, sample, and reagent. Furthermore, a medical provider may not order testing of all relevant HBV markers at once, so that a subject may be called to be tested multiple times. Repeat blood draws are stressful and expensive, and can result in non-compliance and less than optimal treatment. See, e.g., Stramer et al. (2012) *Transfusion* 52:440.

BRIEF SUMMARY OF THE INVENTION

Provided herein are kits for simultaneous detection of multiple Hepatitis B virus (HBV) antibodies in a subject sample so that the HBV status of the subject can be determined. The presently described kits provide a fast, efficient assay for determining if a subject has been exposed to HBV, is suffering HBV infection, has suffered HBV infection in the past, or has been immunized against HBV. Such kits comprise (a) a receptacle comprising or consisting essentially of a mixture of solid supports (e.g., beads, chips, plastic, nitrocellulose, etc.), wherein the mixture includes solid supports conjugated to one of HBsAg, HBcAg, and anti-IgM; and (b) a receptacle comprising conjugate reagent 1 (described below). In some embodiments, the three types of solid supports (e.g., beads) in the mixture are distinguishable from one another (e.g., different sizes, densities, weights, absorbance, reflectance, shape, fluorescence, or other detectable label). In some embodiments, the three types of solid supports in the mixture are each conjugated to a different detectable label, e.g., a fluorescent label or combination of fluorescent labels. In some embodiments, the detectable labels are selected from chromophores, Raman tags, and metal. In some embodiments, the solid supports are magnetically responsive. In some embodiments, the conjugate reagent 1 comprises or consists essentially of labeled HBsAg and labeled HBcAg, wherein the labels on HBsAg and HBcAg are different or the same, and wherein the labels are for indirect detection (e.g., biotin, streptavidin, digitonin, etc.) or direct detection (e.g., fluorophore or luminescent agent).

In some embodiments, the kit further comprises a receptacle comprising conjugate reagent 2. In some embodiments, conjugate reagent 2 comprises or consists essentially of a detectable label conjugated to an agent that specifically binds the labeled HBsAg and labeled HBcAg in conjugate reagent 1. For example, in some embodiments, conjugate reagent 1 comprises or consists essentially of biotinylated HBsAg and biotinylated HBcAg, and conjugate reagent 2 comprises or consists essentially of streptavidin conjugated to a detectable label, e.g., a fluorophore such as phycoerythrin (PE) or fluorescein isothiocyanate (FITC). One of skill will recognize that the streptavidin and biotin can be switched in the previous example, or substituted with another binding pair.

In some embodiments, the kit further comprises at least one internal control, e.g., in receptacle (a), or in a different receptacle to be added to sample. In some embodiments, the internal control is a solid support, e.g., beads, wherein the solid support is conjugated to an agent that will bind analyte known to be in the sample (a sample verification control, e.g., an antibody against a coagulation factor such as FXIII where the sample is blood). As with the other solid supports, the internal control solid support(s) will also be distinguishable, e.g., conjugated to a different detectable label, e.g., a fluorescent label or combination of fluorescent labels. In such embodiments, the conjugate reagent 1 will further comprise a labeled agent to detect agent-analyte binding on the internal control solid support(s), e.g., another antibody against the analyte (e.g., labeled anti-FXIII). In some embodiments, the internal control label(s) is the different or the same, and can be a label for direct or indirect detection. In some embodiments, the internal control is a solid support, e.g., beads, wherein the solid support is conjugated to a detectable label so that is distinguishable from the other solid supports, e.g., a distinct fluorescent label or combination of fluorescent labels (an internal standard control).

In some embodiments, the kit further comprises a container comprising wash reagents (e.g., ready-to-use, a concentrated stock solution, or powder). In some embodiments, the kit further comprises a container comprising materials or reagents for flow cytometry, e.g., buffers, buffer stock solutions or powders, appropriate tubes, etc. In some embodiments, the kit further comprises at least one receptacle comprising at least one calibration control, e.g., for setting the signal level to be considered positive. In some embodiments, the kit includes calibration controls for more than one detectable label, e.g., for the detectable labels on the beads and in the conjugate reagent solution(s). In such cases, the calibration controls can be in one receptacle or more than one receptacle. In some embodiments, the kit includes calibration controls at more than one level for at least one detectable label, e.g., for the detectable labels on the beads and in the conjugate reagent solution(s). In some embodiments, the kit further comprises at least one receptacle comprising a negative control, e.g., with unlabeled beads, or with unlabeled conjugate reagent solution(s).

Further provided are multiplex assays for determining the presence and/or amount of anti-HBs, anti-HBc (total) and anti-HBc (IgM), and thereby determining the HBV infection status of a subject. Accordingly, provided are assays or methods for processing a biological sample from a subject (e.g., mammal, human) comprising (a) contacting the biological sample with a mixture of solid supports (e.g., beads) in a receptacle, wherein the mixture of solid supports comprises (i) solid supports conjugated to HBsAg, (ii) solid supports conjugated to HBcAg, and (iii) solid supports conjugated to anti-IgM (e.g., anti-human IgM); (b) removing non-bead bound components from the receptacle; (c) contacting the mixture of solid supports with conjugate reagent 1; (d) removing non-bead bound components; (e) optionally contacting the mixture of beads with conjugate reagent 2; (f) optionally removing non-bead bound components; and (g) detecting by flow cytometry the detectable labels on the solid supports and in conjugate reagent 1 (or 2 if present). Using the flow cytometry results of step (g), one can determine the presence (positive result) or absence (negative result), and relative amount of anti-HBs, anti-HBc (total) and anti-HBc (IgM) in the biological sample from the subject.

In some embodiments, the three types of solid supports (e.g., beads) in the mixture are distinguishable from one another, e.g., different sizes, densities, weights, absorbance, or detectable labels. In some embodiments, the three types of solid supports in the mixture are each conjugated to a different detectable label, e.g., a fluorescent label or combination of fluorescent labels. In some embodiments, the solid supports are magnetically responsive. In some embodiments, the conjugate reagent 1 comprises or consists essentially of labeled HBsAg and labeled HBcAg, wherein the labels on HBsAg and HBcAg are different or the same, and wherein the labels are for indirect detection (e.g., biotin, streptavidin, digitonin, etc.) or direct detection (e.g., fluorophore or luminescent agent). In some embodiments, conjugate reagent 2 comprises or consists essentially of a detectable label conjugated to an agent that specifically binds the labeled HBsAg and labeled HBcAg in conjugate reagent 1.

In some embodiments, one, two, or all of steps (b), (d), and (f) comprise washing the solid supports to remove non-bead bound components. In some embodiments, the biological sample is selected from blood, blood components (e.g., serum or plasma), or processed blood.

In some embodiments, the assay further comprises detecting by flow cytometry at least one calibration control, wherein positive and negative for one or more detectable labels are determined by comparison to the at least one calibration control. In some embodiments, positive is defined as higher than the calibration control, and negative is defined as lower than the calibration control. In some embodiments, the assay comprises detecting calibration controls for more than one detectable label, e.g., for the detectable labels on the beads and in the conjugate reagent solution(s). In some embodiments, the assay comprises detecting calibration controls at more than one level for at least one detectable label, e.g., for the detectable labels on the beads and in the conjugate reagent solution(s). In some embodiments, the assay further comprises detecting by flow cytometry at least one negative control, e.g., with unlabeled beads, or with unlabeled conjugate reagent solution(s).

In some embodiments the assay further comprises determining that the subject has acute Hepatitis B infection when the detectable label in conjugate reagent 1 (or 2 if present) is positive on solid supports conjugated to IgM. In some embodiments the assay further comprises determining that the subject has been immunized against HBV when the detectable label in conjugate reagent 1 (or 2 if present) is positive on solid supports conjugated to HBsAg, but not on solid supports conjugated to HBcAg or IgM. In some embodiments the assay further comprises determining that the subject has been exposed to HBV (but does not yet have protective immunity) when the detectable label in conjugate reagent 1 (or 2 if present) is positive on solid supports conjugated to HBcAg, but not on solid supports conjugated to HBsAg. In some embodiments the assay further comprises determining that the subject has had an HBV infection in the past when the detectable label in conjugate reagent 1 (or 2 if present) is positive on solid supports conjugated to HBsAg and HBcAg, but not on beads conjugated to IgM.

Further provided are multiplex assays for determining the Hepatitis B infection status of a subject, comprising: (a) contacting a biological sample from the subject with a mixture of beads in a receptacle, wherein the mixture of beads comprises (i) beads conjugated to human Hepatitis B surface antigen (HBsAg) and detectable label (i), (ii) beads conjugated to human Hepatitis B core antigen (HBcAg) and detectable label (ii), and (iii) beads conjugated to an antibody specific for human IgM (anti-IgM) and detectable label (iii); (b) removing non-bead bound components from the receptacle; (c) contacting the mixture of beads with conjugate reagent 1, wherein conjugate reagent 1 comprises: (i) biotinylated HBsAg, and ii) biotinylated HBcAg; (d) removing non-bead bound components; (e) contacting the mixture of beads with conjugate reagent 2, wherein conjugate reagent 2 comprises streptavidin conjugated to detectable label (iv); (f) removing non-bead bound components; and (g) determining by flow cytometry a positive or negative result for detectable label (iv) on beads that are also positive for each of detectable label (i), (ii), or (iii), thereby determining the Hepatitis B infection status of a subject.

In some embodiments, the assay further comprises detecting by flow cytometry at least one calibration control, wherein positive and negative for one or more detectable labels are determined by comparison to the at least one calibration control. In some embodiments, positive is defined as higher than the calibration control, and negative is defined as lower than the calibration control. In some embodiments, the assay comprises detecting by flow cytometry a calibration control for detectable label (iv). In some embodiments, the assay comprises detecting by flow cytometry a calibration control for each of detectable labels (i), (ii), (iii), and (iv).

In some embodiments, step (g) comprises determining that the subject has acute Hepatitis B infection when detectable label (iv) is positive on beads (iii) and optionally on beads (ii). In some embodiments, step (g) comprises determining that the subject has been immunized against Hepatitis B infection when detectable label (iv) is positive on beads (i), but not beads (ii) or (iii). In some embodiments, step (g) comprises determining that the subject has been exposed to Hepatitis B when detectable label (iv) is positive on beads (ii), and optionally beads (iii), but not beads (i). In some embodiments, step (g) comprises determining that the subject has had a past Hepatitis B infection when detectable label (iv) is positive on beads (i) and (ii), but not beads (iii).

In some embodiments, detectable labels (i), (ii), and (iii) are distinct combinations of fluorophores. In some embodiments, detectable label (iv) is selected from PE and FITC.

In some embodiments, beads (i), (ii), and (iii) are magnetically responsive. In some embodiments, one, two, or all of steps (b), (d), and (f) comprise washing the solid supports to remove non-bead bound components. In some embodiments, the biological sample is selected from blood, blood components (e.g., serum or plasma), or processed blood.

DETAILED DESCRIPTION OF THE INVENTION

A. Introduction

Figure 1:
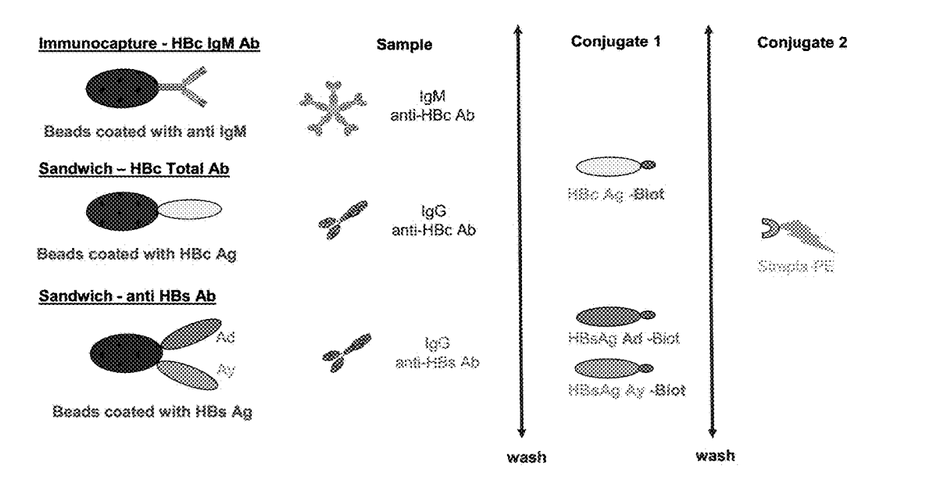
FIG. 1 shows an embodiment of the presently described multiplex HBV assay.

Provided herein are kits, compositions, and methods for simultaneous detection of an infection with a microorganism and/or response to vaccination against the same infection. The process involves the detection of immunoglobulin G (IgG) antibodies to human Hepatitis B surface antigen (anti HBsAg antibodies) in combination with total immunoglobulins (total HBc antibodies) and immunoglobulin M (anti-HBc IgM antibodies) directed against human Hepatitis B core antigen. The presence and amount of each of the antibodies are measured in the same single vessel (tube, well, cuvette, etc.) in the presence of beads. Each bead carries a specific detectable physical parameter (e.g., dye signature), and (1) anti-IgM, (2) HBcAg, or (3) HBsAg. Thus three types of distinctly detectable beads are included in a single vessel to carry out an assay, as shown in FIG. 1. FIG. 1 indicates that the HBsAg beads were coated with the two predominant subtypes of HBsAg, Ad and Ay. Additional subtypes exist, e.g., Aw and Ar (see, e.g., Valet et al. (1975) *CMA J.* 112:1179). One of skill will understand that any one, two, three, four, etc. HBsAg subtypes can be used in any combination in the presently disclosed assays.

The presently described assays offer detection in at least two dimensions, e.g., the identity of the immobilizing bead (e.g., HBsAg, HBcAg, or anti-IgM), and the presence and amount of antibody bound (anti-HBs or anti-HBc). This multidimentional aspect allows for a multiplex format, so that more than one analyte can be detected in a single assay. Moreover, as described below, the inventors have shown that the presently described multiplex assay results successfully correlate with infection status of known patient samples.

The inventors have devised a simple assay, briefly outlined here, for detecting multiple antibodies in a patient sample that are indicative of the presence of an HBV infection, stage of HBV infection, and HBV vaccination status of the patient. In the first step, patient sample, typically blood or a blood component, is contacted with three types of solid supports:

ss1) conjugated to detectable label (e.g., fluorophore) 1 and anti-IgM;

ss2) conjugated to detectable label 2 and HBcAg; and ss3) conjugated to detectable label 3 and HBsAg.

Ss1 will bind all IgM antibodies in the patient sample, regardless of specificity. Ss2 will bind antibodies in the patient sample that are specific for HBcAg, both IgM and IgG. Ss3 will bind antibodies in the patient sample that are specific for HBsAg, predominantly IgG.

After removal of unbound material, labeled HBcAg and HBsAg are added. In the example shown in FIG. 1, the label is biotin, but one of skill will understand that a directly detectable label can be used on the HBcAg and HBsAg to result in a positive or negative signal.

In the present example, after removal of unbound material, detectably labeled streptavidin is added, binds to biotinylated HBcAg and HBsAg, and result in a positive or negative, as well as quantitative, signal. Solid supports 1, 2, and 3 (correlating with detectable labels 1, 2, and 3), and the presence, absence, and quantitative level of signal on each, are detected by flow cytometry. The following Table shows how results can be used to diagnose HBV status of the patient.

|  | Detectable label 1 + (anti-HBc IgM +) | Detectable label 2 + (anti-HBc total +) | Detectable label 3 + (anti-HBs +) |
| --- | --- | --- | --- |
| Not exposed | — | — | — |
| Exposed | — | + | — |
| Acute infection | + | + | — |
| Past infection | — | + | + |
| Immunized | — | — | + |

B. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Springs Harbor Press (Cold Springs Harbor, N Y 1989). The present disclosure refers to items such as labels, solid supports, beads, analytes, etc. according to number or letter (e.g., Detectable label 1, bead (ii), etc.). These numbers and letters are meant to distinguish the item from other items of the same type (e.g., bead (i) vs. bead (ii)), and are not meant to associate a specific property with the number or letter. Any methods, devices and materials similar or equivalent to those described herein can be used in the practice of this invention. The following definitions are provided to facilitate understanding of certain terms used frequently herein and are not meant to limit the scope of the present disclosure.

Multiplex assays are analyses that simultaneously measure the levels of more than one analyte in a single sample. Multiplex assay methods and reagents are described, e.g., in U.S. Pat. No. 6,773,578 and WO2008148883.

The term "solid support" is used herein to denote a solid inert surface or body to which an agent, such as an antibody or an antigen can be immobilized. Non-limiting examples include plastic, nitrocellulose, membranes chips, and particles. The term "immobilized" as used herein denotes a molecular-based coupling that is not significantly de-coupled under the conditions imposed during the steps of the assays described herein. Such immobilization can be achieved through a covalent bond, an ionic bond, an affinity-type bond, or any other chemical bond.

The term "particle" is used herein to refer to a solid or semisolid body, often with linear dimensions on the micron scale (i.e., less than 100 microns), of any shape or surface texture. Except as noted, the term is used interchangeably with "microparticle," which refers to a micron scale particle, and "bead," which refers to particles that are spherical or near-spherical in shape, often polymeric in composition.

The terms "receptacle," "vessel," "tube," "well," etc. refer to a container that can hold reagents or an assay. If the receptacle is in a kit and holds reagents, it will typically be closed or sealed. If the receptacle is being used for an assay, it will typically be open or accessible during steps of the assay.

The term "biological sample" encompasses a variety of sample types obtained from an organism. The term encompasses bodily fluids such as blood, blood components, saliva, serum, plasma, urine and other liquid samples of biological origin, solid tissue biopsy, tissue cultures, or supernatant taken from cultured patient cells. In the context of the present disclosue, the biological sample is typically a bodily fluid with detectable amounts of antibodies, e.g., blood or a blood component. The biological sample can be processed prior to assay, e.g., to remove cells or cellular debris. The term encompasses samples that have been manipulated after their procurement, such as by treatment with reagents, solubilization, sedimentation, or enrichment for certain components.

The term "antibody" as used herein refers to a polypeptide encoded by an immunoglobulin gene or immunoglobulin genes, or fragments thereof, which specifically bind and recognize an analyte (antigen). The recognized immunoglobulin light chains are classified as either kappa or lambda. Immunoglobulin heavy chains are classified as gamma, mu, alpha, delta, or epsilon, which in turn define the immunoglobulin classes, IgG, IgM, IgA, IgD and IgE, respectively.

An example of a structural unit of immunoglobulin G (IgG antibody) is a tetramer. Each such tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains, respectively.

Antibodies exist as intact immunoglobulins or as well-characterized fragments produced by digestion of intact immunoglobulins with various peptidases. Thus, for example, pepsin digests an antibody near the disulfide linkages in the hinge region to produce F(ab')2, a dimer of Fab which itself is a light chain joined to VH—CH1 by a disulfide bond. The F(ab')2 dimer can be reduced under mild conditions to break the disulfide linkage in the hinge region, thereby converting the F(ab')2 dimer into two Fab' monomers. The Fab' monomer is essentially an Fab with part of the hinge region (see, Paul (Ed.), *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or by de novo synthesis using recombinant DNA methodologies such as single chain Fv.

Antibodies are commonly referred to according their targets. While the nomenclature varies, one of skill in the art will be familiar and understand that several names can be applied to the same antibody. For example, an antibody specific for IgM can be called "anti-IgM," "IgM antibody," "anti-IgM antibody," etc.

The terms "antigen," "immunogen," "antibody target," "target analyte," and like terms are used herein to refer to a molecule, compound, or complex that is recognized by an antibody, i.e., can be specifically bound by the antibody. The term can refer to any molecule that can be specifically recognized by an antibody, e.g., a polypeptide, polynucleotide, carbohydrate, lipid, chemical moiety, or combinations thereof (e.g., phosphorylated or glycosylated polypeptides, etc.). One of skill will understand that the term does not indicate that the molecule is immunogenic in every context, but simply indicates that it can be targeted by an antibody.

Antibodies bind to an "epitope" on an antigen. The epitope is the localized site on the antigen that is recognized and bound by the antibody. Epitopes can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The terms "specific for," "specifically binds," and like terms refer to a molecule (e.g., antibody or antibody fragment) that binds to its target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, an antibody that specifically binds a given antibody target will typically bind the antibody target with at least a 2-fold greater affinity than a non-antibody target. Specificity can be determined using standard methods, e.g., solid-phase ELISA immunoassays (see, e.g., Harlow & Lane, *Using Antibodies, A Laboratory Manual* (1998) for a description of immunoassay formats and conditions that can be used to determine specific immunoreactivity).

The term "binds" with respect to an antibody target (e.g., antigen, analyte), typically indicates that an antibody binds a majority of the antibody targets in a pure population (assuming appropriate molar ratios). For example, an antibody that binds a given antibody target typically binds to at least ⅔ of the antibody targets in a solution (e.g., at least any of 75, 80, 85, 90, 91, 92, 93, 94, 95, 96, 97, 98, 99, or 100%). One of skill will recognize that some variability will arise depending on the method and/or threshold of determining binding.

The terms "label," "detectable label, "detectable moiety," and like terms refer to a composition detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA), biotin, digoxigenin, $^{32}P$ and other isotopes, haptens, and proteins which can be made detectable, e.g., by incorporating a radiolabel into the peptide or used to detect antibodies specifically reactive with the peptide. The term includes combinations of single labeling agents, e.g., a combination of fluorophores that provides a unique detectable signature, e.g., at a particular wavelength or combination of wavelengths. Any method known in the art for conjugating label to a desired agent may be employed, e.g., using methods described in Hermanson, *Bioconjugate Techniques* 1996, Academic Press, Inc., San Diego.

The term "positive," when referring to a result or signal, indicates the presence of an analyte or item that is being detected in a sample. The term "negative," when referring to a result or signal, indicates the absence of an analyte or item that is being detected in a sample. Positive and negative are typically determined by comparison to at least one control, e.g., a threshold level that is required for a sample to be determined positive, or a negative control (e.g., a known blank).

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters, and will understand which controls are valuable in a given situation and be able to analyze data based on comparisons to control values. Controls are also valuable for determining the significance of data. For example, if values for a given parameter are variable in controls, variation in test samples will not be considered as significant.

A "calibration control" is similar to a positive control, in that it includes a known amount of a known analyte. In the case of a multiplex assay, the calibration control can be designed to include known amounts of multiple known analytes. The amount of analyte(s) in the calibration control can be set at a minimum cut-off amount, e.g., so that a higher amount will be considered "positive" for the analyte(s), while a lower amount will be considered "negative" for the analyte(s). In some cases, multilevel calibration controls can be used, so that a range of analyte amounts can be more accurately determined. For example, an assay can include calibration controls at known low and high amounts, or known minimal, intermediate, and maximal amounts.

The term "diagnosis" refers to a relative probability that a subject has an infection, disorder or disease. Similarly, the term "prognosis" refers to a relative probability that a certain future outcome may occur in the subject. For example, in the context of the present disclosure, prognosis can refer to the likelihood that an individual will be infected in the future (e.g., unlikely if immunized). The terms are not intended to be absolute, as will be appreciated by any one of skill in the field of medical diagnostics.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc.

C. Multiplex Assays

The presently described assays involve detection of more than one analyte in a single assay, and are thus described as multiplex assays. The presently described assays include components for immobilizing multiple analytes on distinguishable solid supports so that each of the multiple analytes can be identified and quantified by flow cytometry. Assay components and considerations include the solid supports and how to distinguish the different types of solid supports from one another (e.g., labels or other differentiation parameters), components to specifically immobilize the desired analytes and remove other sample materials, and labels for detecting and quantifying the desired analytes.

The presently described multiplex assays involve use of a solid support, typically particles (also referred to as microparticles or beads). For detection by flow cytometry, particles that emit autofluorescence should be avoided since this will increase background signal and render them unsuitable. Particles created by standard emulsion polymerization from a variety of starting monomers generally exhibit low autofluorescence, while those that have been modified to increase porosity ("macroporous" particles) exhibit high autofluorescence. Autofluorescence in such particles further increases with increasing size and increasing percentage of divinylbenzene monomer.

Within these limitations, the size range of the microparticles can vary and particular size ranges are not critical. In most cases, the aggregated size range of the microparticles lies within the range of from about 0.3 micrometers to about 100 micrometers in particle diameter, e.g., within the range of from about 0.5 micrometers to about 40 micrometers Magnetic particles are commonly used in the art, and can make separation and wash steps more convenient for the presently described assays. "Magnetic particles," "magnetically responsive material," "magnetic beads," and like terms denote a material that responds to a magnetic field. Magnetically responsive materials include paramagnetic materials (e.g., iron, nickel, and cobalt, as well as metal oxides such as $Fe_3O_4$, $BaFe_{12}O_{19}$, CoO, NiO, $Mn_2O_3$, $Cr_2O_3$, and CoMnP), ferromagnetic materials, ferrimagnetic materials, and metamagnetic materials. Rather than constituting the entire microparticle, the magnetically responsive material typically constitutes one component of the microparticle, while the remainder consists of a polymeric material which can be chemically derivatized to permit attachment of an assay reagent (e.g., antigen or antibody).

Methods of, and instrumentation for, applying and removing a magnetic field as part of an assay are known to those skilled in the art and reported in the literature. Examples of literature reports are Forrest et al., U.S. Pat. No. 4,141,687; Ithakissios, U.S. Pat. No. 4,115,534; Vlieger et al., *Analytical Biochemistry* 205:1-7 (1992); Dudley, *Journal of Clinical Immunoassay* 14:77-82 (1991); and Smart, *Journal of Clinical Immunoassay* 15:246-251 (1992).

The polymeric matrix that forms the microparticle can be any material that is compatible with the presently described assays. The matrix should be inert to the components of the biological sample and to the assay reagents, have minimal autofluorescence, be solid and insoluble in the sample and in any other reagents or washes used in the assay, and capable of affixing an assay reagent to the microparticle. Examples of suitable polymers are polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle.

Functional groups for attachment of the assay reagent (e.g., antigen or antibody) can be incorporated into the polymer structure by conventional means. Examples of suitable functional groups are amine groups, ammonium groups, hydroxyl groups, carboxylic acid groups, and isocyanate groups. The assay reagent is typically covalently bound to the solid phase surface, either directly or indirectly, e.g., with a linking group. Linking groups can be used as a means of increasing the density of reactive groups on the solid phase surface and decreasing steric hindrance to increase the range and sensitivity of the assay, or as a means of adding specific types of reactive groups to the solid phase surface to broaden the range of types of assay reagents that can be affixed to the solid phase. Examples of suitable useful linking groups are polylysine, polyaspartic acid, polyglutamic acid and polyarginine.

Microparticles of different types in a multiplex assay can be distinguished from one another, e.g., by size, weight, light scatter or absorbance, reflectance, shape, or label, e.g., fluorescent label.

Where microparticle size is used as a differentiation factor (distinguishing characteristic), the widths of the size subranges and the spacing between mean diameters of adjacent subranges are selected to permit differentiation of different types of microparticles by flow cytometry, as will be apparent to those skilled in the use of and instrumentation for flow cytometry. Typically, a subrange for a given mean diameter is about ±5% CV or less of the mean diameter, where CV is the coefficient of variation and is defined as the standard deviation of the particle diameter divided by the mean particle diameter times 100 percent. The mean diameters of subranges for different types of particles are generally spaced apart by at least about 6% of the mean diameter of one of the subranges, e.g., at least about 8% or 10% of the mean diameter of one of the subranges.

Light scatter can also be used to distinguish different types of microparticles. Side angle light scatter varies with particle size, granularity, absorbance and surface roughness, while forward angle light scatter is mainly affected by size and refractive index. Varying any of these qualities can result in light scatter differences that can serve as a means of distinguishing the various groups.

Still another example of a differentiation parameter is absorbance. When light is applied to particles, the absorbance of the light by the particles is indicated mostly by a change in the strength of the laterally (side-angle) scattered light while the strength of the forward-scattered light is relatively unaffected. Consequently, the difference in absorbance between various colored dyes associated with the particles is determined by observing differences in the strength of the laterally scattered light.

A wide array of parameters or characteristics can be used as differentiation parameters to distinguish the particles of one group from those of another. The differentiation parameters may arise from particle size, composition, physical characteristics that affect light scattering, excitable fluorescent dyes or colored dyes that impart different emission spectra and/or scattering characteristics to the particles, or from different concentrations of one or more fluorescent dyes.

When the distinguishable characteristic is a fluorescent dye or color, it can be coated on the surface of the microparticle, embedded in the microparticle, or bound to the molecules of the microparticle material. Thus, fluorescent microparticles can be manufactured by combining the polymer material with the fluorescent dye, or by impregnating the microparticle with the dye. Microparticles with dyes already incorporated and thereby suitable for use in the present invention are commercially available, from suppliers such as Spherotech, Inc. (Libertyville, Ill., USA) and Molecular Probes, Inc. (Eugene, Oreg., USA). A list of vendors of flow cytometric products can be found, e.g., at the website of molbio.princeton.edu/facs/FCMsites.html.

Labels can be any substance or component that directly or indirectly emits or generates a detectable signal. In some embodiments, the labels are fluorophores, many of which are reported in the literature and thus known to those skilled in the art, and many of which are readily commercially available. Literature sources for fluorophores include Cardullo et al., *Proc. Natl. Acad. Sci. USA* 85: 8790-8794 (1988); Dexter, *J. of Chemical Physics* 21: 836-850 (1953); Hochstrasser et al., *Biophysical Chemistry* 45: 133-141 (1992); Selvin, *Methods in Enzymology* 246: 300-334 (1995); Steinberg, Ann. Rev. Biochem., 40: 83-114 (1971); Stryer, *Ann. Rev. Biochem.* 47: 819-846 (1978); Wang et al., *Tetrahedron Letters* 31: 6493-6496 (1990); and Wang et al., *Anal. Chem.* 67: 1197-1203 (1995).

The following are examples of fluorophores that can be used as labels:
4-acetamido-4'-isothiocyanatostilbene-2,2'disulfonic acid
acridine
acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate N-(4-anilino-1-naphthyl)maleimide
anthranilamide
BODIPY
Brilliant Yellow
coumarin
7-amino-4-methylcoumarin (AMC, Coumarin 120)
7-amino-4-trifluoromethylcoumarin (Coumaran 151)
cyanine dyes
cyanosine
4',6-diaminidino-2-phenylindole (DAPI)
5', 5"-dibromopyrogallol-sulfonaphthalein (Bromopyrogallol Red)
7-diethylamino-3-(4'-isothiocyanatophenyl)-4-methylcoumarin diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin
eosin isothiocyanate
erythrosin B
erythrosin isothiocyanate
ethidium
5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)
fluorescein
fluorescein isothiocyanate
fluorescamine
IR144
IR1446
Malachite Green isothiocyanate
4-methylumbelliferone
ortho cresolphthalein
nitrotyrosine
pararosaniline
Phenol Red
phycoerythrin (including but not limited to B and R types)
o-phthaldialdehyde
pyrene pyrene butyrate
succinimidyl 1-pyrene butyrate
quantum dots
Reactive Red 4 (Cibacron™ Brilliant Red 3B-A)
6-carboxy-X-rhodamine (ROX)
6-carboxyrhodamine (R6G)
lissamine rhodamine B sulfonyl chloride rhodamine
rhodamine B
rhodamine 123
rhodamine X isothiocyanate
sulforhodamine B
sulforhodamine 101
sulfonyl chloride derivative of sulforhodamine 101 (Texas Red)
N,N,N',N'-tetramethyl-6-carboxyrhodamine (TAMRA)
tetramethyl rhodamine
tetramethyl rhodamine isothiocyanate (TRITC)
riboflavin
rosolic acid
lanthanide chelate derivatives A prominent group of fluorophores for immunoassays are fluorescein, fluorescein isothiocyanate, phycoerythrin, rhodamine B, and Texas Red (sulfonyl chloride derivative of sulforhodamine 101). Any of the fluorophores in the list preceding this paragraph can be used in the presently described assays, either to label the microparticle, or to label a binding agent (e.g., an antibody or streptavidin). Fluorochromes can be attached by conventional covalent bonding, using appropriate functional groups on the fluorophores and on the microparticle or binding agent. The recognition of such groups and the reactions to form the linkages will be readily apparent to those skilled in the art.

Other labels that can be used in place of the fluorophores are radioactive labels and enzyme labels. These are likewise known in the art.

Flow cytometry methods and instrumentation are known in the art. Descriptions of instrumentation and methods can be found, e.g., in Introduction to Flow Cytometry: A Learning Guide (2000) Becton, Dickinson, and Company; McHugh, "Flow Microsphere Immunoassay for the Quantitative and Simultaneous Detection of Multiple Soluble Analytes," Methods in Cell Biology 42, Part B (Academic Press, 1994).

D. Examples

This example illustrates performance of an embodiment of the presently described HBV multiplex assay on a set of 46 plasma samples from human subjects. Nine samples were from HBV-vaccinated patients, and 37 samples were from patients showing symptoms of HBV infection. Patient samples were tested for the presence of anti-HBs, anti-HBc (total), and anti-HBc (IgM) using the BioPlex 2200 assay. Readings were obtained by flow cytometry, which is able to detect each bead according to its fluorescent dye signature, as well as the presence of antibody bound to each bead. HBsAg beads bind all antibodies (primarily IgG) that bind HBsAg. HBcAg beads bind all antibodies (primarily IgG and IgM) that bind HBcAg. Anti-IgM beads bind all IgM antibodies, including those specific for HBcAg. All beads are magnetic. Bead reagent was prepared from 8 uL of each of: BioSpacific Ad/Ay (HBsAg)-coated beads (10 mg/ml stock); Steenvoorde HBc 309-coated beads (10 mg/ml stock); and Medix anti-mu coated beads (10 mg/ml stock)+2 ml particle diluent. In addition, 2 control beads were included with each assay: Internal Standard Bead (ISB) (10 mg/ml stock) and Serum Verification Bead (SVB) (10 mg/ml stock). The ISB is designed to identify detector fluctuation(s), and is coated with a unique fluorescent dye, in this case called tetra methyl rhodamine cadaverine (TMRC). The SVB is designed to confirm the presence of serum or plasma in the sample and is coated with anti-FXIII (coagulation factor XIII).

Each sample was incubated with bead reagent, unbound sample components were removed, and the now-coupled beads were washed. Conjugate Reagent 1, comprising biotinylated reporter antigens and biotinylated reporter antibody was added. The reporter antigens include a domain for recognition and binding to the bead-bound antibodies, and a detectable moiety, for either direct or indirect detection. In this case, reporter antigens and antibody were Biotinylated HBs Ad (0.6 mg/ml stock), Biotinylated HBs Ay (0.58 mg/ml stock), Biotinylated HBc307(0.55 mg/ml stock), and Biotinylated anti-FXIII (1.17 mg/ml stock). Concentrations in Conjugate Reagent 1 were 1.25 ug/ml, 1.25 ug/ml, and 0.2 ug/ml, and 0.1 ug/ml, respectively. Again, unbound reagents were removed, the coupled beads washed, and Conjugate Reagent 2 was added. Conjugate Reagent 2 included streptavidin-PE (1.0 mg/ml stock) at a concentration of 6.0 ug/ml. In this case, the Conjugate Reagents included 1% trehalose and 0.5% CHAPS, as buffering and background control reagents, but one of skill will understand that different reagents can be used for these purposes. After washing, samples were resuspended and signal detected by flow cytometry.

Control and calibration values were established as shown in Table 1.

TABLE 1

Control and cutoff calibrator RFI signals for multiplex HBV assay

|  | Anti-HBs | Anti-HBc (total) | Anti-HBc (IgM) |
| --- | --- | --- | --- |
| HBs_NC<br>Negative control for anti-HBs assay | 102 | 59 | 67 |
| HBs_Cal<br>Cut-off calibrator for anti-HBs assay | 381 | 59 | 60 |
| HBc_NC<br>Negative control for anti-HBc (total) and anti-HBc (IgM) assays | 76 | 50 | 83 |
| HBc_Cal<br>Cut-off calibrator for anti-HBc (total) assay | 77 | 221 | 99 |
| HBcIgM_Cal<br>Cut-off calibrator for anti-HBc (IgM) assay | 81 | 6840 | 2148 |

Once control and calibration values were set, patient samples were tested. Prior to testing, patients were categorized as (i) acute infection, (ii) exposed to HBV, (iii) susceptible, (iv) past infection, and (v) immunized.

TABLE 2

Raw patient data for multiplex HBV assay

|  | Anti-HBs | | Anti-HBc (total) | | Anti-HBc (IgM) | | |
| --- | --- | --- | --- | --- | --- | --- | --- |
| Sample ID | Signal | S/CO | Signal | S/CO | Signal | S/CO | Status |
| 65255 | 48 | 0.1 | 1031 | 4.7 | 12460 | 5.8 | Acute Infection |
| 66311B | 59 | 0.2 | 564 | 2.6 | 982 | 0.5 | Exposed to HBV |
| 65973 | 61 | 0.2 | 1063 | 4.8 | 27401 | 12.8 | Acute Infection |
| 66673 | 61 | 0.2 | 4405 | 20.0 | 25543 | 11.9 | Acute Infection |

TABLE 2-continued

Raw patient data for multiplex HBV assay

| Sample ID | Anti-HBs Signal | S/CO | Anti-HBc (total) Signal | S/CO | Anti-HBc (IgM) Signal | S/CO | Status |
|---|---|---|---|---|---|---|---|
| 66760 | 65 | 0.2 | 4365 | 19.8 | 26763 | 12.5 | Acute Infection |
| KB72168 | 65 | 0.2 | 4224 | 19.2 | 28809 | 13.4 | Acute Infection |
| U66398 | 66 | 0.2 | 2235 | 10.1 | 15284 | 7.1 | Acute Infection |
| 63906 | 67 | 0.2 | 1590 | 7.2 | 15204 | 7.1 | Acute Infection |
| 66761 | 67 | 0.2 | 3451 | 15.7 | 25968 | 12.1 | Acute Infection |
| U66545 | 67 | 0.2 | 2068 | 9.4 | 15457 | 7.2 | Acute Infection |
| 66073 | 69 | 0.2 | 1592 | 7.2 | 27098 | 12.6 | Acute Infection |
| 66311 | 70 | 0.2 | 1387 | 6.3 | 15042 | 7.0 | Acute Infection |
| 66392 | 70 | 0.2 | 2042 | 9.3 | 19036 | 8.9 | Acute Infection |
| U66546 | 71 | 0.2 | 2053 | 9.3 | 13631 | 6.3 | Acute Infection |
| U66541 | 73 | 0.2 | 2640 | 12.0 | 15758 | 7.3 | Acute Infection |
| 66544 | 75 | 0.2 | 2247 | 10.2 | 16657 | 7.8 | Acute Infection |
| 65936 | 76 | 0.2 | 1816 | 8.2 | 28248 | 13.2 | Acute Infection |
| U66075 | 76 | 0.2 | 2337 | 10.6 | 23647 | 11.0 | Acute Infection |
| U66458 | 77 | 0.2 | 2477 | 11.2 | 23036 | 10.7 | Acute Infection |
| 67492 | 79 | 0.2 | 5843 | 26.5 | 28121 | 13.1 | Acute Infection |
| U66525 | 80 | 0.2 | 8141 | 36.9 | 27705 | 12.9 | Acute Infection |
| 66672 | 81 | 0.2 | 5706 | 25.9 | 28489 | 13.3 | Acute Infection |
| 1365146-24 | 83 | 0.2 | 84 | 0.4 | 1287 | 0.6 | Susceptible |
| 1365146-21 | 96 | 0.3 | 8121 | 36.8 | 189 | 0.1 | Exposed to HBV |
| 1257146-9 | 125 | 0.3 | 13377 | 60.7 | 449 | 0.2 | Exposed to HBV |
| 67403 | 126 | 0.3 | 3183 | 14.4 | 27296 | 12.7 | Acute Infection |
| 1257146-5 | 130 | 0.3 | 21928 | 99.4 | 178 | 0.1 | Exposed to HBV |
| 1257146-3 | 141 | 0.4 | 19368 | 87.8 | 165 | 0.1 | Exposed to HBV |
| 1257146-8 | 142 | 0.4 | 23585 | 107.0 | 166 | 0.1 | Exposed to HBV |
| 65579 | 171 | 0.4 | 12411 | 56.3 | 2763 | 1.3 | Acute Infection |
| 1365146-48 | 175 | 0.5 | 786 | 3.6 | 163 | 0.1 | Exposed to HBV |
| U65370 | 200 | 0.5 | 1774 | 8.0 | 27122 | 12.6 | Acute Infection |
| 1365146-51 | 227 | 0.6 | 3495 | 15.9 | 151 | 0.1 | Exposed to HBV |
| 65471 | 279 | 0.7 | 1641 | 7.4 | 16979 | 7.9 | Acute Infection |
| 65480 | 685 | 1.8 | 60 | 0.3 | 89 | 0.0 | Immunized |
| U65501 | 739 | 1.9 | 48 | 0.2 | 436 | 0.2 | Immunized |
| 67421 | 823 | 2.2 | 55 | 0.2 | 52 | 0.0 | Immunized |
| U65499 | 1834 | 4.8 | 131 | 0.6 | 175 | 0.1 | Immunized |
| 1365146-46 | 4325 | 11.4 | 10223 | 46.4 | 261 | 0.1 | Past Infection |
| U65498 | 5234 | 13.8 | 50 | 0.2 | 113 | 0.1 | Immunized |
| 65487 | 18886 | 49.6 | 54 | 0.2 | 177 | 0.1 | Immunized |
| 67433 | 23311 | 61.3 | 58 | 0.3 | 189 | 0.1 | Immunized |
| 67439 | 23811 | 62.6 | 54 | 0.2 | 257 | 0.1 | Immunized |
| 1365146-52 | 28505 | 74.9 | 1435 | 6.5 | 203 | 0.1 | Past Infection |
| 65477 | 29027 | 76.3 | 50 | 0.2 | 68 | 0.0 | Immunized |
| 1365146-45 | 30485 | 80.1 | 3757 | 17.0 | 667 | 0.3 | Past Infection |

For data interpretation, "reactive" (positive) was set at a sample signal/cutoff (S/CO) calibrator signal of ≥1.0, while "non-reactive" (negative) was set at a sample S/CO calibrator signal of ≤1.0. Table 3 shows interpretation of the raw results using the S/CO scores above.

TABLE 3

Processed results for multiplex HBV assay

| Sample ID | Anti-HBs | Anti-HBc Total | Anti-HBc IgM | Interpretation |
|---|---|---|---|---|
| 65255 | Non-Reactive | Reactive | Reactive | Acute Infection |
| 66311B | Non-Reactive | Reactive | Non-Reactive | Exposed to HBV |
| 65973 | Non-Reactive | Reactive | Reactive | Acute Infection |
| 66673 | Non-Reactive | Reactive | Reactive | Acute Infection |
| 66760 | Non-Reactive | Reactive | Reactive | Acute Infection |
| KB72168 | Non-Reactive | Reactive | Reactive | Acute Infection |
| U66398 | Non-Reactive | Reactive | Reactive | Acute Infection |
| 63906 | Non-Reactive | Reactive | Reactive | Acute Infection |
| 66761 | Non-Reactive | Reactive | Reactive | Acute Infection |
| U66545 | Non-Reactive | Reactive | Reactive | Acute Infection |
| 66073 | Non-Reactive | Reactive | Reactive | Acute Infection |
| 66311 | Non-Reactive | Reactive | Reactive | Acute Infection |
| 66392 | Non-Reactive | Reactive | Reactive | Acute Infection |
| U66546 | Non-Reactive | Reactive | Reactive | Acute Infection |

TABLE 3-continued

Processed results for multiplex HBV assay

| Sample ID | Anti-HBs | Anti-HBc Total | Anti-HBc IgM | Interpretation |
|---|---|---|---|---|
| U66541 | Non-Reactive | Reactive | Reactive | Acute Infection |
| 66544 | Non-Reactive | Reactive | Reactive | Acute Infection |
| 65936 | Non-Reactive | Reactive | Reactive | Acute Infection |
| U66075 | Non-Reactive | Reactive | Reactive | Acute Infection |
| U66458 | Non-Reactive | Reactive | Reactive | Acute Infection |
| 67492 | Non-Reactive | Reactive | Reactive | Acute Infection |
| U66525 | Non-Reactive | Reactive | Reactive | Acute Infection |
| 66672 | Non-Reactive | Reactive | Reactive | Acute Infection |
| 1365146-24 | Non-Reactive | Non-Reactive | Non-Reactive | Susceptible |
| 1365146-21 | Non-Reactive | Reactive | Non-Reactive | Exposed to HBV |
| 1257146-9 | Non-Reactive | Reactive | Non-Reactive | Exposed to HBV |
| 67403 | Non-Reactive | Reactive | Reactive | Acute Infection |
| 1257146-5 | Non-Reactive | Reactive | Non-Reactive | Exposed to HBV |
| 1257146-3 | Non-Reactive | Reactive | Non-Reactive | Exposed to HBV |
| 1257146-8 | Non-Reactive | Reactive | Non-Reactive | Exposed to HBV |
| 65579 | Non-Reactive | Reactive | Reactive | Acute Infection |
| 1365146-48 | Non-Reactive | Reactive | Non-Reactive | Exposed to HBV |
| U65370 | Non-Reactive | Reactive | Reactive | Acute Infection |
| 1365146-51 | Non-Reactive | Reactive | Non-Reactive | Exposed to HBV |
| 65471 | Non-Reactive | Reactive | Reactive | Acute Infection |
| 65480 | Reactive | Non-Reactive | Non-Reactive | Immunized |
| U65501 | Reactive | Non-Reactive | Non-Reactive | Immunized |
| 67421 | Reactive | Non-Reactive | Non-Reactive | Immunized |
| U65499 | Reactive | Non-Reactive | Non-Reactive | Immunized |
| 1365146-46 | Reactive | Reactive | Non-Reactive | Past Infection |
| U65498 | Reactive | Non-Reactive | Non-Reactive | Immunized |
| 65487 | Reactive | Non-Reactive | Non-Reactive | Immunized |
| 67433 | Reactive | Non-Reactive | Non-Reactive | Immunized |
| 67439 | Reactive | Non-Reactive | Non-Reactive | Immunized |
| 1365146-52 | Reactive | Reactive | Non-Reactive | Past Infection |
| 65477 | Reactive | Non-Reactive | Non-Reactive | Immunized |
| 1365146-45 | Reactive | Reactive | Non-Reactive | Past Infection |

The above examples are provided to illustrate the invention but not to limit its scope. Other variants of the invention will be readily apparent to one of ordinary skill in the art and are encompassed by the appended claims. All publications, databases, internet sources, patents, patent applications, and accession numbers cited herein are hereby incorporated by reference in their entirety for all purposes.

What is claimed is:

1. A multiplex assay for processing a biological sample from a human subject comprising:
   (a) contacting the biological sample with a mixture of beads in a receptacle, wherein the mixture of beads comprises:
      (i) beads conjugated to human Hepatitis B surface antigen (HBsAg) and detectable label (i),
      (ii) beads conjugated to human Hepatitis B core antigen (HBcAg) and detectable label (ii), and
      (iii) beads conjugated to an antibody specific for human IgM (anti-IgM) and detectable label (iii);
   (b) removing non-bead bound components from the receptacle;
   (c) contacting the mixture of beads with conjugate reagent 1, wherein conjugate reagent 1 comprises:
      (i) biotinylated HBsAg, and
      (ii) biotinylated HBcAg;
   (d) removing non-bead bound components;
   (e) contacting the mixture of beads with conjugate reagent 2, wherein conjugate reagent 2 comprises streptavidin conjugated to detectable label (iv);
   (f) removing non-bead bound components; and
   (g) determining by flow cytometry a positive or negative result for detectable label (iv) on beads that are also positive for each of detectable label (i), (ii), or (iii), thereby processing the biological sample from the human subject.

2. The assay of claim 1, wherein detectable labels (i), (ii), and (iii) are distinct combinations of fluorophores.

3. The assay of claim 1, wherein detectable label (iv) is selected from phycoerythrin and fluorescein isothiocyanate.

4. The assay of claim 1, wherein beads (i), (ii), and (iii) are magnetically responsive.

5. The assay of claim 1, wherein step (b), step (d), and/or step (f) comprises washing the beads.

6. The assay of claim 1, wherein positive and negative are determined by comparison to a calibration control, positive is defined as higher than the calibration control, and negative is defined as lower than the calibration control.

7. The assay of claim 1, further comprising determining that the subject has acute Hepatitis B infection when detectable label (iv) is positive on beads (iii).

8. The assay of claim 1, further comprising determining that the subject has been immunized against Hepatitis B infection when detectable label (iv) is positive on beads (i), but not beads (ii) or (iii).

9. The assay of claim 1, further comprising determining that the subject has been exposed to Hepatitis B when detectable label (iv) is positive on beads (ii), but not beads (i) or (iii).

10. The assay of claim 1, further comprising determining that the subject has had a past Hepatitis B infection when detectable label (iv) is positive on beads (i) and (ii), but not beads (iii).

11. The assay of claim 1, wherein the biological sample is blood, a blood component, or processed blood.

12. A multiplex assay for determining the Hepatitis B infection status of a subject, comprising:
(a) contacting a biological sample from the subject with a mixture of beads in a receptacle, wherein the mixture of beads comprises:
  (i) beads conjugated to human Hepatitis B surface antigen (HBsAg) and detectable label (i),
  (ii) beads conjugated to human Hepatitis B core antigen (HBcAg) and detectable label (ii), and
  (iii) beads conjugated to an antibody specific for human IgM (anti-IgM) and detectable label (iii);
(b) removing non-bead bound components from the receptacle;
(c) contacting the mixture of beads with conjugate reagent 1, wherein conjugate reagent 1 comprises:
  (i) biotinylated HBsAg, and
  (ii) biotinylated HBcAg;
(d) removing non-bead bound components;
(e) contacting the mixture of beads with conjugate reagent 2, wherein conjugate reagent 2 comprises streptavidin conjugated to detectable label (iv);
(f) removing non-bead bound components; and
(g) determining by flow cytometry a positive or negative result for detectable label (iv) on beads that are also positive for each of detectable label (i), (ii), or (iii), thereby determining the Hepatitis B infection status of a subject.

13. The assay of claim 12, wherein positive and negative are determined by comparison to a calibration control, positive is defined as higher than the calibration control, and negative is defined as lower than the calibration control.

14. The assay of claim 12, wherein step (g) comprises:
determining that the subject has acute Hepatitis B infection when detectable label (iv) is positive on beads (iii);
determining that the subject has been immunized against Hepatitis B infection when detectable label (iv) is positive on beads (i), but not beads (ii) or (iii);
determining that the subject has been exposed to Hepatitis B when detectable label (iv) is positive on beads (ii), but not beads (i) or (iii); and
determining that the subject has had a past Hepatitis B infection when detectable label (iv) is positive on beads (i) and (ii), but not beads (iii).

15. The assay of claim 12, wherein detectable labels (i), (ii), and (iii) are distinct combinations of fluorophores.

16. The assay of claim 12, wherein detectable label (iv) is selected from phycoerythrin and fluorescein isothiocyanate.

17. The assay of claim 12, wherein beads (i), (ii), and (iii) are magnetically responsive.

18. The assay of claim 12, wherein step (b), step (d), and/or step (f) comprises washing the beads.

19. The assay of claim 12, wherein the biological sample is blood, a blood component, or processed blood.

* * * * *